(12) United States Patent
Ohnishi et al.

(10) Patent No.: US 7,758,753 B2
(45) Date of Patent: Jul. 20, 2010

(54) METHOD OF ANALYZING OPTICAL ISOMERS OR METHOD OF RESOLVING THE SAME

(75) Inventors: Atsushi Ohnishi, Himeji (JP); Akito Ichida, Otake (JP)

(73) Assignee: Daicel Chemical Industries, Ltd., Osaka-shi, Osaka (JP)

( * ) Notice: Subject to any disclaimer, the term of this patent is extended or adjusted under 35 U.S.C. 154(b) by 28 days.

(21) Appl. No.: 12/226,855

(22) PCT Filed: Jul. 22, 2007

(86) PCT No.: PCT/JP2007/063055
§ 371 (c)(1),
(2), (4) Date: Oct. 30, 2008

(87) PCT Pub. No.: WO2007/148834
PCT Pub. Date: Dec. 27, 2007

(65) Prior Publication Data
US 2009/0166292 A1 Jul. 2, 2009

(30) Foreign Application Priority Data
Jun. 23, 2006 (JP) .............................. 2006-173971

(51) Int. Cl.
*B01D 15/08* (2006.01)
(52) U.S. Cl. ...................... 210/635; 210/656; 210/198.2
(58) Field of Classification Search ................. 210/635, 210/656, 659, 198.2, 502.1; 436/161; 73/61.57
See application file for complete search history.

(56) References Cited

U.S. PATENT DOCUMENTS 5,496,927 A   3/1996   Kolb et al.
5,496,937 A   3/1996   Okamoto et al.
5,679,572 A   10/1997  Okamoto et al.
2004/0149660 A1  8/2004  Kasuya et al.
2006/0189796 A1  8/2006  Okamoto et al.

FOREIGN PATENT DOCUMENTS

| JP | 03-073851 | 3/1991 |
|----|-----------|--------|
| JP | 07-005160 | 1/1995 |
| JP | 11-255671 | * 9/1999 |

OTHER PUBLICATIONS

PTO Translation No. 10-2109 of Japan Patent No. 11-255671.*
Ekitai Chromatography Q&A 100, Study Basic Theory and Technology through Examples, by I. Matsushita, 2000 Nen 6 Gatsu 25 Nichi Hakko, Gihodo Shuppan Co., Ltd., Hakko, pp. 40-41.

(Continued)

*Primary Examiner*—Ernest G Therkorn
(74) *Attorney, Agent, or Firm*—Flynn, Thiel, Boutell & Tanis, P.C.

(57) ABSTRACT

Provided are a method of quickly and simply confirming the success or failure of resolution of optical isomers with the use of a column for resolving optical isomers and a method of simply designing the conditions of the eluent composition under isocratic elution conditions. In resolving optical isomers, the success or failure of the resolution can be simply and quickly confirmed by employing an HPLC gradient elution analysis method with the use of a column for resolving optical isomers. When the resolution is successfully conducted, the eluent composition under isocratic elution conditions can be estimated from the elution time in the gradient elution analysis.

8 Claims, 6 Drawing Sheets

OTHER PUBLICATIONS

Anaylsis of Enantiomeric Flavanones in Plant Extracts by High-Performance Liquid Chromatography on a Cellulose Triacetate Based Chiral Stationary Phase, by M. Krause et al, Chromatographia vol. 32, No. 1/2, Jul. 1991, pp. 69-72.

Separation of benz[f]isoindole derivatives of amino acid and amino acid amide enantiomers on a β-cyclodextrin-bonded phase, by A.L.L. Duchateau et al, Journal of Chromatography, vol. 63, 1992, pp. 151-156.

* cited by examiner

METHOD OF ANALYZING OPTICAL ISOMERS OR METHOD OF RESOLVING THE SAME

TECHNICAL FIELD

The present invention relates to a method of analyzing optical isomers or a method of resolving the optical isomers.

BACKGROUND ART

Conventionally, in HPLC (high performance liquid chromatography) analysis, isocratic analysis in which elution occurs with a solvent of a fixed composition and gradient analysis in which elution occurs while changing with time a mobile phase composition are employed. In the isocratic analysis, a stable chromatogram is obtained. However, in the isocratic analysis, it sometimes takes a long time to resolve components which are different in the retentivity to a stationary phase, or the peak may be broadened. In contrast, in the gradient analysis, by changing the composition ratio of a mobile phase and increasing an elution ability, analysis time can be shortened and broadening of the peak can be suppressed.

Various resolving agents and columns are commercially available as a stationary phase for resolving optical isomers. As such resolving agents for optical isomers, used frequently are polysaccharide derivatives which demonstrates excellent resolution properties in resolving various compounds. Moreover, in recent years, a solvent-resistant resolving agent for optical isomers has been developed which can be used under mobile phase conditions of a polar solvent and, in which isomers a polysaccharide derivative has been immobilized on a carrier (Patent Documents 1 and 2). A column for resolving optical isomers, which has been charged with the polysaccharide-based solvent-resistant resolving agent, has drawn attention because various solvents has become available as a mobile phase while high resolution properties of the polysaccharide derivatives are maintained. However, a trial-and-error procedure is required for achieving sharp resolution in a short time (preferably 30 minutes or shorter).

Patent Document 1: JP 2751003 A

Patent Document 2: JP 2751004 A

DISCLOSURE OF THE INVENTION

Problems to be Solved by the Invention

The present invention provides a simple analyzing method or a simple resolving method using a solvent-resistant column for resolving optical isomers for use in HPLC in which a polysaccharide derivative is used as an asymmetry recognition agent.

Means for Solving the Problems

The inventors of the present invention have extensively studied, and, as a result, found that analysis conditions for achieving favorable resolution can be simply obtained by gradient analysis and that conditions of isocratic analysis can be easily determined from gradient analysis results. Thus, the present invention has been accomplished.

That is, the present invention provides a method of analyzing or resolving an optical isomer, including:

resolving the optical isomer from a mixture of optical isomers by a gradient elution method using a solvent of two or more components and using a solvent-resistant column for resolving an optical isomer for use in HPLC in which a polysaccharide derivative is used as an asymmetry recognition agent.

In addition, the present invention provides a method of analyzing or resolving an optical isomer, including: based on an elution time of a first peak (t1) obtained by the gradient analysis of claim 1, resolving an optical isomer under isocratic conditions and at a composition ratio obtained by multiplying a solvent composition ratio at the time of t1 calculated from a gradient inclination by a factor (f1).

According to the present invention, the gradient analysis makes it possible to rapidly and simply confirm the possibility of asymmetry recognition by a solvent-resistant column for resolving optical isomers for use in HPLC in which a polysaccharide derivative is used as an asymmetry recognition agent. Moreover, conditions of isocratic analysis or resolution for precise analysis or fraction can be easily determined.

BEST MODE FOR CARRYING OUT THE INVENTION

Figure 1:
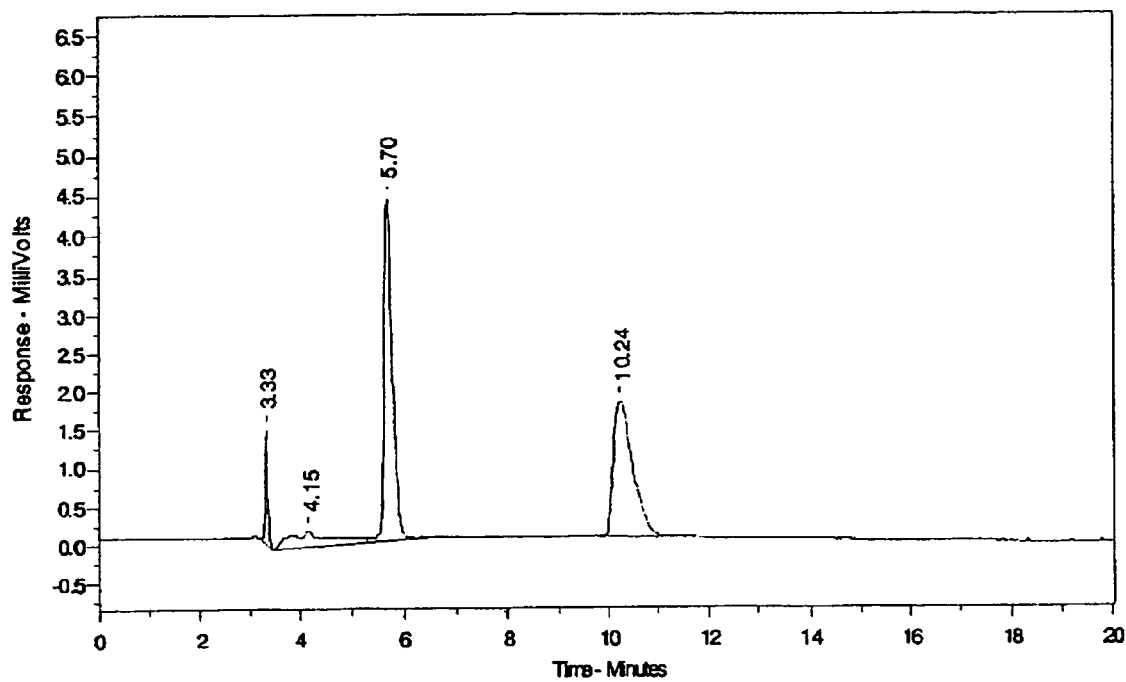
FIG. 1 is a chromatogram obtained in Example 1.

Hereinafter, the present invention will be described in detail according to embodiments of the present invention. Commercially-available HPLC apparatuses can be used.

A polysaccharide derivative is used as an asymmetry recognition agent for use in the present invention. Examples of polysaccharide include cellulose and amylose.

In the present invention, the polysaccharide derivative refers to a substance in which the hydroxy group of polysaccharide is modified. Preferable examples of the polysaccharide derivative include carbamate derivatives or ester derivatives having an aromatic substituent. Still more preferable examples thereof include carbamate derivatives or ester derivatives having an alkylated aromatic group. Particularly preferable examples of the polysaccharide derivative include amylose tris(3,5-dimethylphenylcarbamate) and cellulose tris(3,5-dimethylphenylcarbamate).

Derivatization of the polysaccharide in the present invention is performed by known methods. For example, as described in WO 95/23125 and the like, the polysaccharide derivative can be produced through dehydration or the like of polysaccharide with a compound which can be reacted with a hydroxy group of polysaccharide and which includes the above-mentioned functional group or becomes the above-mentioned functional group through the reaction with the hydroxy group.

The solvent-resistant column for resolving optical isomers for use in HPLC in which the polysaccharide derivative in the present invention is used as an asymmetry recognition agent refers to a column for HPLC (high performance liquid chromatography) which has been charged with a filler for resolving a solvent-resistant optical isomer containing the polysaccharide derivative.

Here, the filler for resolving a solvent-resistant optical isomer containing the polysaccharide derivative refers to a substance in which the above-mentioned polysaccharide derivative is immobilized on a carrier. The immobilization can be performed by the methods described in Patent Documents 1 and 2, and, moreover, JP 2002-148247 A, JP 2004-167343 A, or WO 04/095018.

The column for HPLC which has been charged with the thus-obtained filler for resolving a solvent-resistant optical isomer is commercially available as, for example, Chiral Pack IA, Chiral Pack IB, and the like from Daicel Chemical Industries, Ltd.

In gradient analysis, the solvent mixing ratio of a mobile phase, the solvent composition ratio of a mobile phase, ionic strength, pH, etc. are changed with time to a convex shape, a linear shape, and a concave shape. Preferably, the solvent composition ratio of a mobile phase is changed to a linear shape. The solvent composition for use in a gradient elution method is a solvent composition of two or more components containing a combination of a low polar solvent such as hexane and a high polar solvent (excluding alcohols such as methanol, ethanol, and 2-propanol) such as THF (tetrahydrofuran) and acetone; a solvent composition of two or more components containing a combination of a low polar solvent such as hexane and a medium polar solvent such as chloroform; a solvent composition of two or more components containing a combination of a medium polar solvent and a high polar solvent; or a solvent composition of three or more components containing a combination of a low polar solvent, a medium polar solvent, and a high polar solvent. To a solvent used for the gradient elution method, either or both of amine compounds such as diethylamine or/and acid compounds such as trifluoroacetic acid and acetic acid may be added in a proportion of from 0.01 to 5.0%.

Next, a method of determining isocratic conditions from gradient analysis data will be described. First, in the case where a compound is eluted during the gradient analysis, based on the elution time (t1) of the first peak obtained by the gradient analysis, the solvent composition ratio at the time of elution (t1) of the first peak is calculated from the determined gradient inclination (V). Among the obtained solvent composition ratios, the ratio of a solvent having a lower ratio under initial conditions (a higher polar solvent) is multiplied by a factor (f1) to obtain a composition ratio (C). The isocratic conditions are determined based on the composition ratio (C) (Equation 1).

This factor is suitably determined in the range of from 0.8 to 0.1 in view of the elution time of the first peak, a resolution factor, and a difference between the determined gradient curve and an actual gradient curve. In order to achieve favorable resolution in a short period of time, the factor is preferably within the range of from 0.5 to 0.1.

$$C=(A+V\times t1)\times f1 \quad \text{(Equation 1)}$$

A: Initial composition ratio (%) of a solvent which is to be subjected to gradient (a solvent having a lower ratio under initial conditions)

V: Gradient inclination of a solvent (%/min)

C: Composition ratio (%) of a solvent which has been subjected to gradient under isocratic conditions (a solvent having a lower ratio under initial conditions)

In contrast, in the case where a compound is eluted after completion of the gradient, the ratio of a solvent having a lower ratio under initial conditions among solvent ratios at the time of completion of the gradient is multiplied by 0.2 to calculate the isocratic ratio (B) (Equation 3). The isocratic conditions are determined based on the composition ratio (D) obtained by multiplying a difference between the elution time (t1) of the first peak and a time (Gt) required for the gradient by a factor (f2) (Equation 2). The factor (f2) is within the range of 4 to 30, and preferably within the range of 5 to 20.

$$D=B+(t1-Gt)\times f2 \quad \text{(Equation 2)}$$

$$B=(A+V\times Gt)\times 0.2 \quad \text{(Equation 3)}$$

A: Initial composition ratio (%) of a solvent which is to be subjected to gradient (a solvent having a lower ratio under initial conditions)

B: Ratio obtained by converting a solvent composition ratio at the time of completion of gradient in terms of isocratic conditions V: Gradient inclination of a solvent (%/min)

Gt: Gradient time (min)

D: Composition ratio (%) of a solvent which has been subjected to gradient under isocratic conditions (a solvent having a lower ratio under initial conditions)

EXAMPLES

Hereinafter, the present invention will be described in more detail with reference to examples, but is not limited to those examples. HPLC analysis is performed using a chromatography data processing system: Chrom Perfect manufactured by Justice Laboratory Softare, a chromatography control system: BOWIN manufactured by Nippon Bunko Co., Ltd., a liquid chromatography pump: PU-1580 manufactured by Nippon Bunko Co., Ltd., a UV detector for liquid chromatography: PU-1575 manufactured by Nippon Bunko Co., Ltd., an autosampler for liquid chromatography: PU-1555 manufactured by Nippon Bunko Co., Ltd., a mixing machine for liquid chromatography: HG1580-32 manufactured by Nippon Bunko Co., Ltd., and a degasser for liquid chromatography: or DG1580-53 manufactured by Nippon Bunko Co., Ltd.

Example 1

Using a column manufactured by Daicel Chemical Industries, Ltd. (Registered trademark: Chiral Pack IA (0.46 cm$\phi$× 25 cmL)) as a column for resolving an optical isomer and using a hexane/THF mixed solvent as a mobile phase, t-stilbene oxide was divided at a flowrate of 1.0 ml/min at a temperature of 25° C. During the process, analysis was performed while increasing the THF ratio (v/v) in the mobile phase from 5% to 95% over 18 minutes. The first peak eluted at 6.30 minutes, and the second peak eluted at 11.20 minutes. The resolution factor (a) was 2.48. The THF amount in the mobile phase when the first peak eluted was about 37% (5%+ 5%×6.30=36.5%). The ratio was multiplied by 0.2 as a factor (f1) to thereby determine the THF ratio in an isocratic mobile phase (hexane/THF=93/7), whereby baseline resolution was achieved in a short time. The results are shown in Table 1 and FIG. 1.

Example 2

Figure 2:
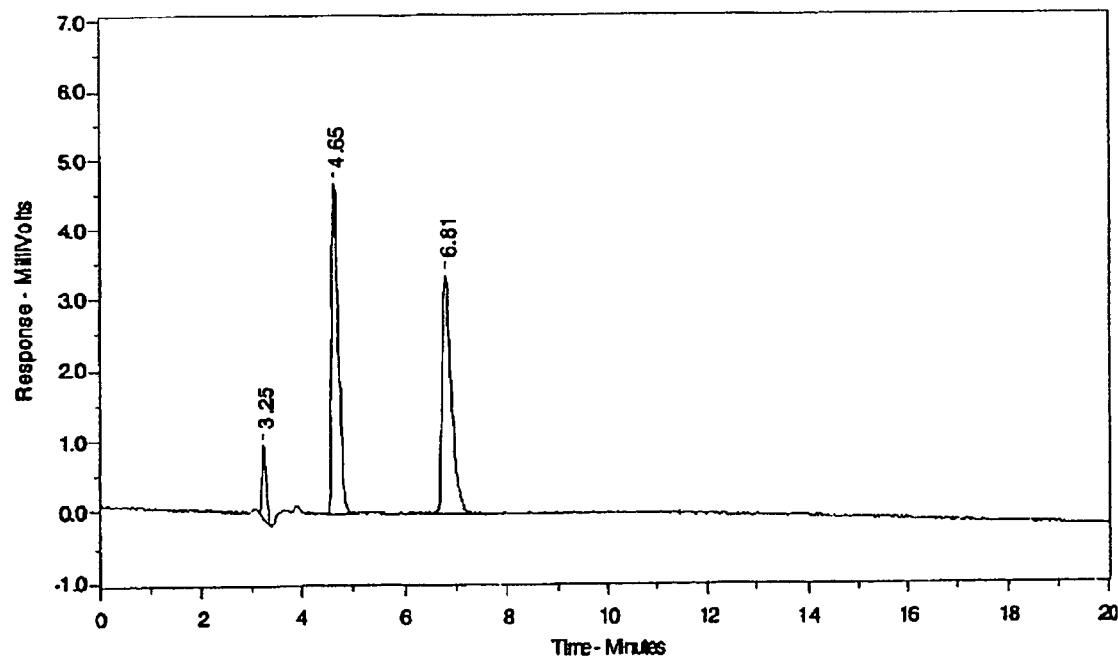
FIG. 2 is a chromatogram obtained in Example 2.

By multiplying 0.33 as a factor (f1) of Example 2 to determine the THF ratio in an isocratic mobile phase (hexane/THF=88/12), baseline resolution was achieved in a short time. The results are shown in Table 1 and FIG. 2.

Comparative Example 1

Figure 3:
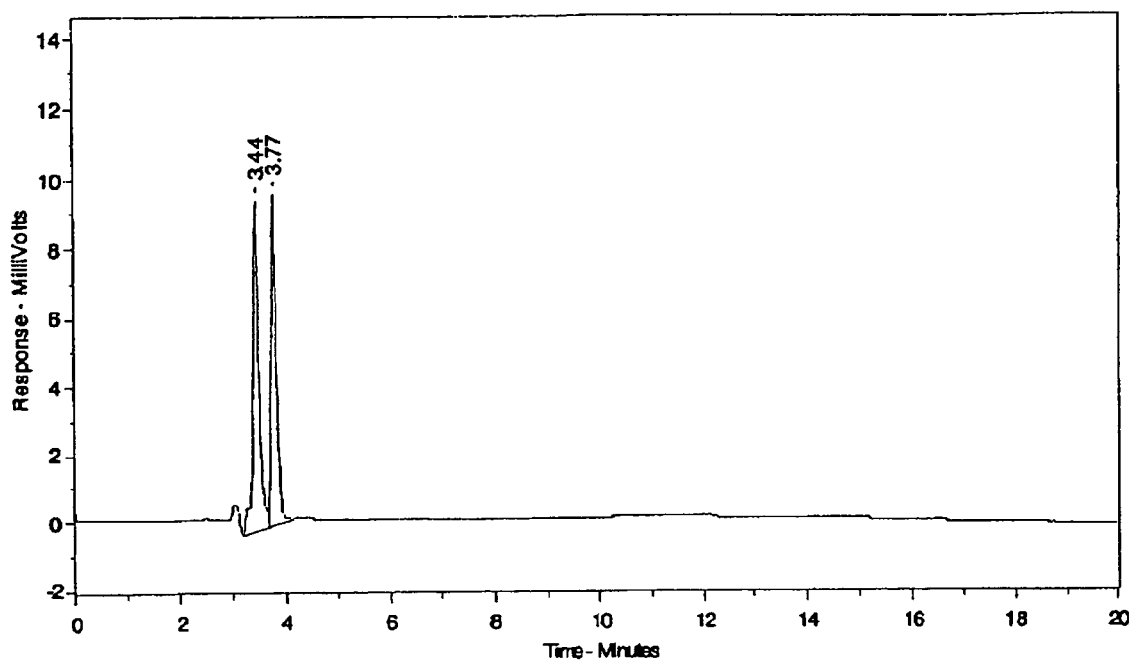
FIG. 3 is a chromatogram obtained in Comparative Example 1.

By multiplying 1 as a factor (f1) of Example 1 to determine the THF ratio (hexane/THF=63/37), and resolution was performed. Complete resolution was achieved with difficulty. The results are shown in Table 1 and FIG. 3.

TABLE 1

| | | | | Ratio at the time of the elution of | | | Resolution under isocratic conditions | | | |
|---|---|---|---|---|---|---|---|---|---|---|
| | T1 (min) | T2 (min) | a | the first peak (Hexane/THF) | Example | Factor (f1) | Mobile phase (Hexane/THF) | T1 (min) | T2 (min) | a |
| Compound t-stilbene oxide | 6.3 | 11.2 | 2.48 | 63/37 | Example 1 (FIG. 1) | 0.2 | 93/7 | 5.7 | 10.24 | 2.68 |
| | | | | | Example 2 (FIG. 2) | 0.33 | 88/12 | 4.65 | 6.81 | 2.31 |
| | | | | | Comparative Example 1 (FIG. 3) | 1 | 63/37 | 3.47 | 3.77 | 1.75 |

Example 3

Figure 4:
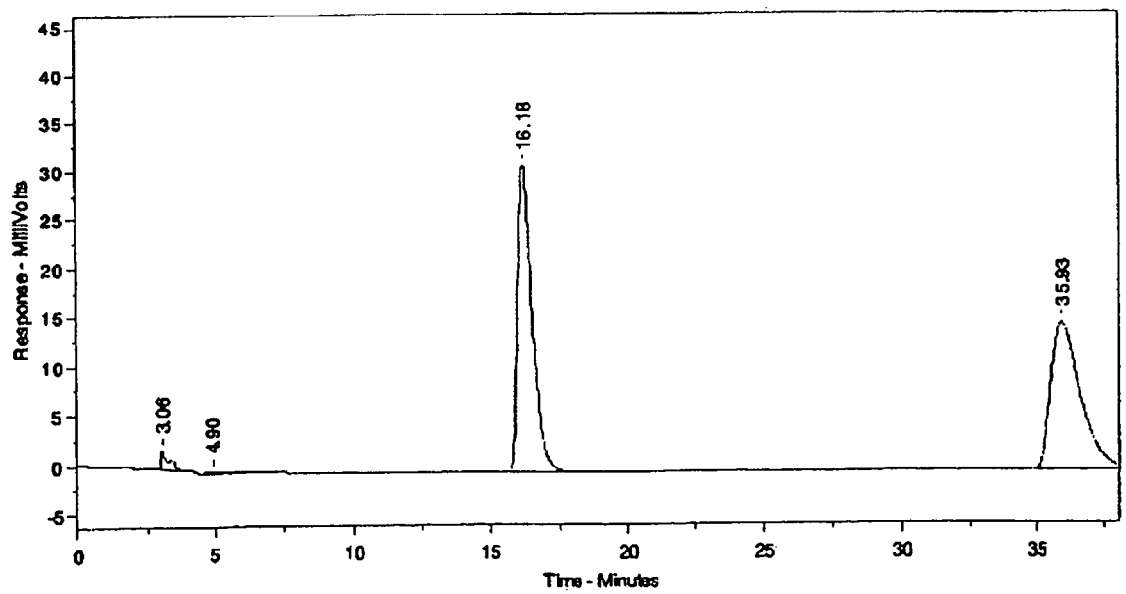
FIG. 4 is a chromatogram obtained in Example 3.

Using a column manufactured by Daicel Chemical Industries, Ltd. (Registered trademark: Chiral Pack IA (0.46 cmϕ× 25 cmL)) as a column for resolving an optical isomer and using a hexane/THF mixed solvent as a mobile phase, aminoglutethimide was divided at a flow rate of 1.0 ml/min at a temperature of 25° C. During the process, the THF ratio (v/v) in the mobile phase was increased from 5% to 95% over 18 minutes. Dipping was continued while maintaining the composition ratio at the time of completion of the gradient. The first peak of aminoglutethimide eluted 20.0 minutes after pouring, and the second peak eluted 21.78 minutes after pouring. The resolution factor (a) was 1.42. Based on the results of this gradient analysis, the THF ratio at the time of the elution of the first peak was converted to the ratio (B) in terms of isocratic. The ratio (B) was 95×0.2=19. The isocratic conditions (hexane/THF=68/32) were determined based on the composition ratio (D) obtained by adding, to the ratio (B), a value obtained by multiplying a difference between the elution time (t1) of the first peak and a time (Gt) required for gradient by 6.5 (factor (f2)). Thus, favorable resolution was achieved. The results are shown in Table 2 and FIG. 4.

Example 4

Figure 5:
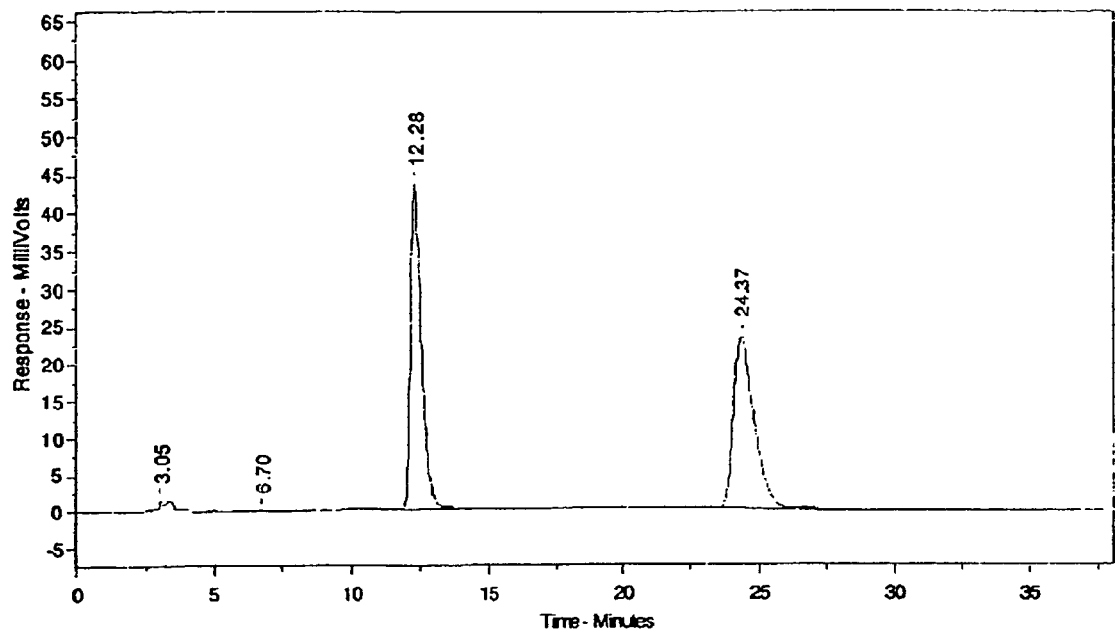
FIG. 5 is a chromatogram obtained in Example 5.

In Example 3, the isocratic conditions (hexane/THF=64/36) were determined based on the composition ratio (D) obtained by adding a value obtained by multiplying a difference between the elution time (t1) of the first peak and a time (Gt) required for gradient by 8.5 (factor (f2)). Thus, favorable resolution was achieved. The results are shown in Table 2 and FIG. 5.

Comparative Example 2

Figure 6:
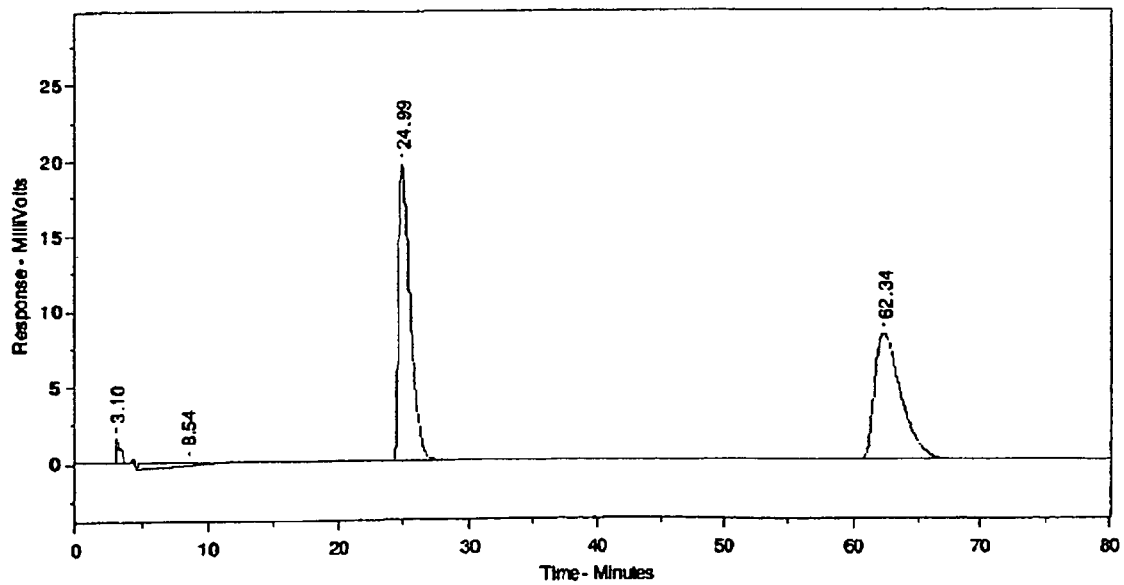
FIG. 6 is a chromatogram obtained in Comparative Example 2.

In Example 3, the isocratic conditions (hexane/THF=72/28) were determined based on the composition ratio (D) obtained by adding a value obtained by multiplying a difference between the elution time (t1) of the first peak and a time (Gt) required for gradient by 4.5 (factor (f2)). Thus, complete resolution was achieved. The elution time of the first peak was as long as 25 minutes. The results are shown in Table 2 and FIG. 6.

TABLE 2

| | Resolution under gradient conditions *1 | | | | | Ratio (B) obtained by converting THF ratio at the time of completion of gradient in terms of isocratic | | Resolution under isocratic conditions | | | |
|---|---|---|---|---|---|---|---|---|---|---|---|
| | T1 (min) | T2 (min) | a | Ratio at the time of completion of gradient (Hexane/THF) | Example | | Factor (f2) | Mobile phase (Hexane/THF(D)) | T1 (min) | T2 (min) | a |
| Compound Aminoglutethimide | 20 | 21.78 | 1.42 | 5/95 | Example 3 (FIG. 4) | 19 | 6.5 | 68/32 | 16.18 | 35.93 | 2.55 |
| | | | | | Example 4 (FIG. 5) | | 8.5 | 64/36 | 12.28 | 24 | 2.3 |
| | | | | | Comparative Example 2 (FIG. 6) | | 4.5 | 72/28 | 24.99 | 62.34 | 2.7 |

*1: Gradient Time 18 min

Example 5

Figure 7:
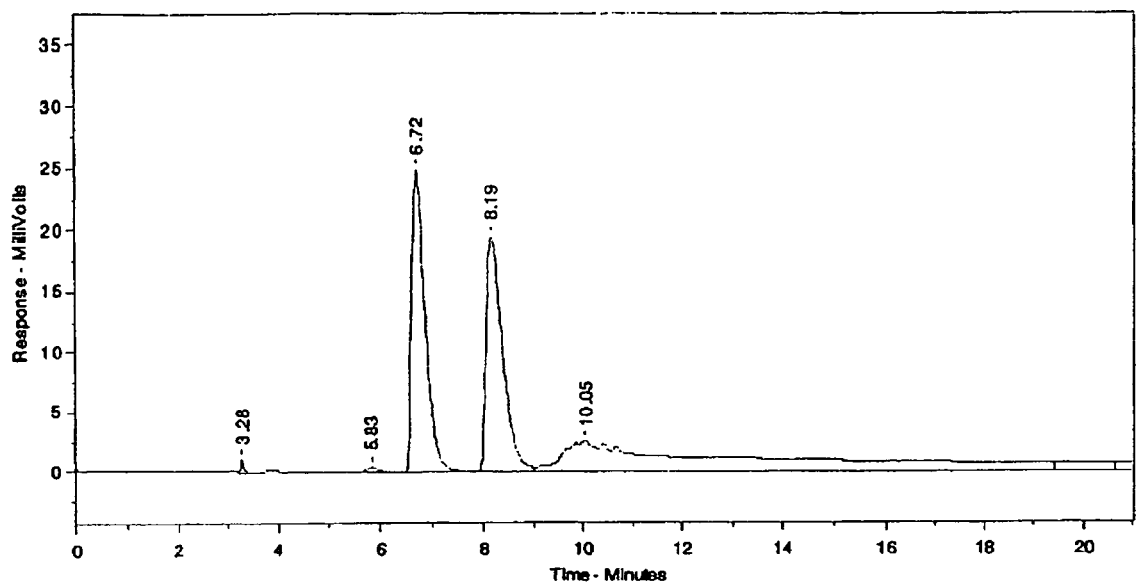
FIG. 7 is a chromatogram obtained in Example 5.

The isocratic conditions were determined in the same manner as in Example 1 using a traeger base as a compound. The results are shown in Table 3, and the chromatogram is shown in FIG. 7.

Example 6

Figure 8:
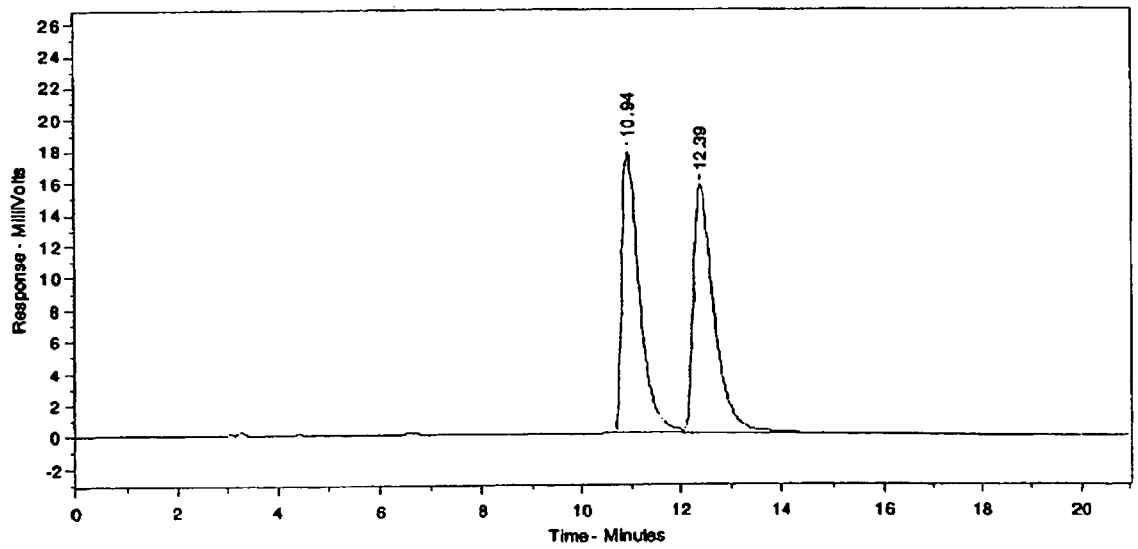
FIG. 8 is a chromatogram obtained in Example 6.

The isocratic conditions were determined in the same manner as in Example 1 using 1,1'-2-binaphtol as a compound. The results are shown in Table 3, and the chromatogram is shown in FIG. 8.

Example 7

Figure 9:
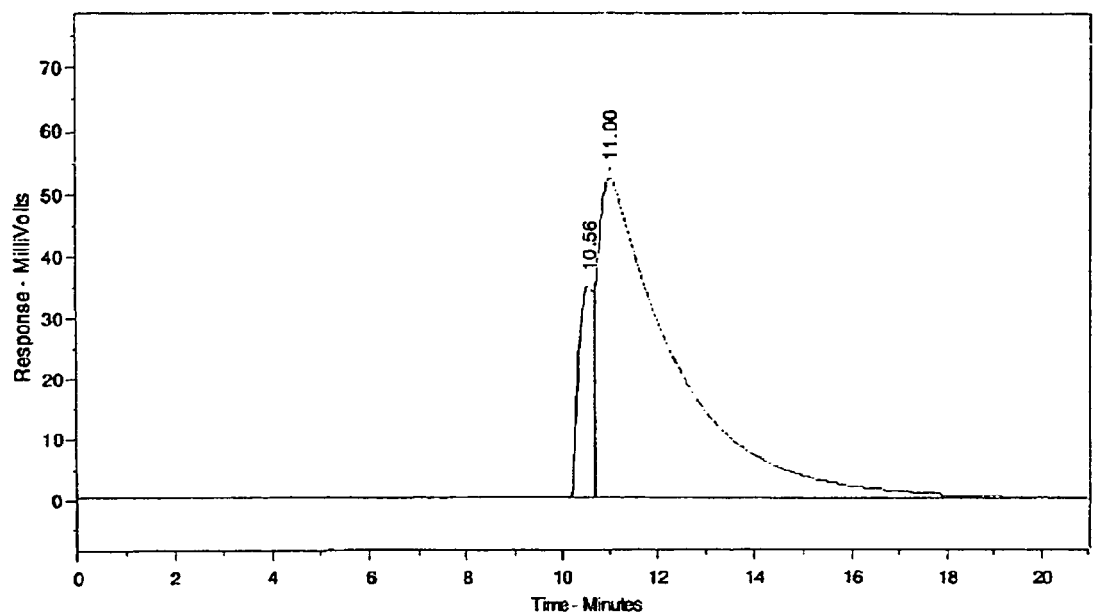
FIG. 9 is a chromatogram obtained in Example 7.

The isocratic conditions were determined in the same manner as in Example 1 using cobalt acetylacetonate as a compound. The results are shown in Table 3, and the chromatogram is shown in FIG. 9.

TABLE 3

| | Resolution under gradient conditions | | | | | | Resolution under isocratic conditions | | | |
|---|---|---|---|---|---|---|---|---|---|---|
| | | | | Ratio at the time of the elution of | | | | | | |
| Compound | T1 (min) | T2 (min) | a | the first peak (Hexane/THF) | Example | Factor (f1) | Mobile phase (Hexane/THF) | T1 (min) | T2 (min) | a |
| Traeger base | 9.6 | 11.31 | 1.26 | 47/53 | Example 5 (FIG. 7) | 0.2 | 89/11. | 6.72 | 8.19 | 1.4 |
| 1,1'-2-binaphtol | 14.61 | 14.99 | 1.03 | 22/78 | Example 6 (FIG. 8) | 0.2 | 84/16 | 10.94 | 12.39 | 1.18 |
| Cobalt acetylacetonate | 14.09 | 14.09 | 1 | 25/75 | Example 7 (FIG. 9) | 0.2 | 85/15 | 10.56 | 11.06 | 1.06 |

*1: Gradient Time 18 min

Example 8

Figure 10:
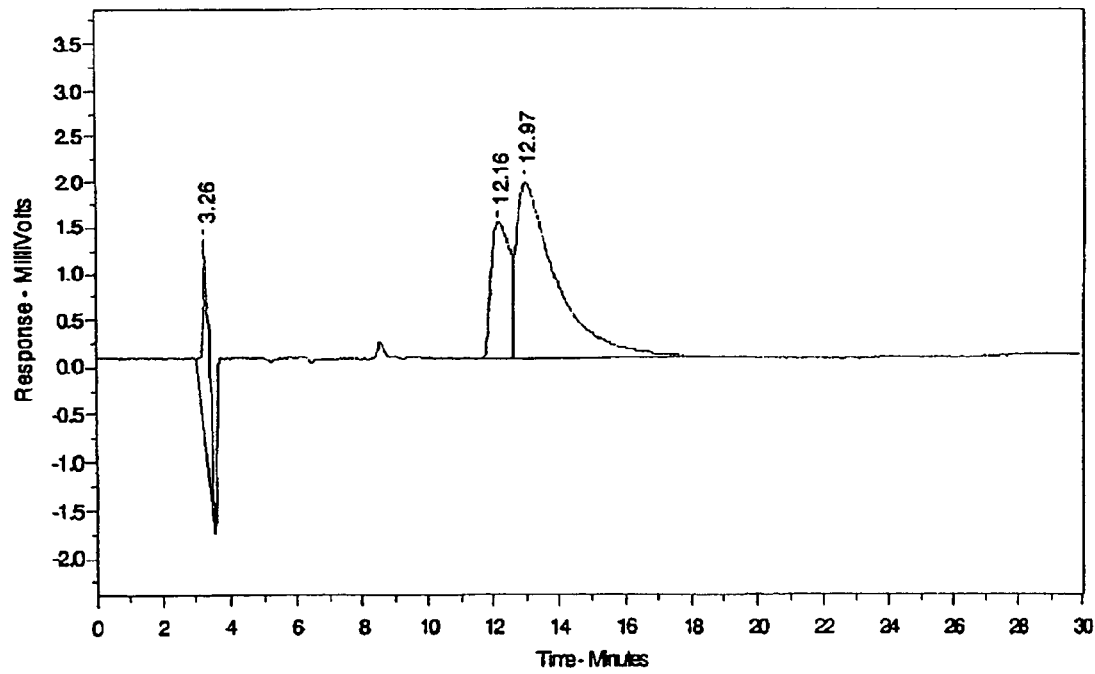
FIG. 10 is a chromatogram obtained in Example 8.

In Example 1, using a hexane/ethyl acetate (AcOEt)/diethylamine (DEA) mixed solvent as a mobile phase, a compound, laudanosine, was divided. During the process, analysis was performed while fixing the DEA ratio to 0.1% and increasing the AcOEt ratio (v/v) from 5% to 95% over 18 minutes. As a result, resolution hardly occurred, and the peak eluted at 15.27 minutes. The AcOEt in the mobile phase at the time of the elution of the peak was expressed by the equation: 5%+5%×15.27=81.35%. The ratio was multiplied by 0.2 as a factor (f1) to thereby determine the THF ratio in an isocratic mobile phase (hexane/AcOEt/DEA=84/16/0.1), whereby partial resolution was achieved. The results are shown in Table 4 and FIG. 10.

(DEA) mixed solvent. During the process, the CHCl3 ratio (v/v) in the mobile phase was increased from 5% to 95% over 18 minutes. Dipping was continued while maintaining the composition ratio at the time of completion of gradient. The first peak of aminoglutethimide eluted 26.68 minutes after pouring, and the second peak eluted 32.96 minutes after pouring. The resolution factor (a) was 1.27. Based on the results of this gradient analysis, the CHCl3 ratio at the time of the elution of the first peak was converted to the ratio (B) in terms of isocratic. The ratio was 95×0.2=19. The isocratic conditions (hexane/CHCl3/DEA=25/75/0.1) were determined based on the composition ratio (D) obtained by adding, to the ratio (B), a value obtained by multiplying a difference

TABLE 4

| | Resolution under gradient conditions | | | | | | Resolution under isocratic conditions | | | |
|---|---|---|---|---|---|---|---|---|---|---|
| | | | | Ratio at the time of the elution of | | | | | | |
| Compound | T1 (min) | T2 (min) | a | the first peak (Hexane/*THF/DEA) | Example | Factor (f1) | Mobile phase (Hexane/THF) | T1 (min) | T2 (min) | a |
| Laudanosine | 15.27 | 15.57 | | 19/81/0.1 | Example 8 (FIG. 10) | 0.2 | 84/16 | 12.16 | 12.97 | 1.09 |

*Gradient solvent

Example 9

Figure 11:
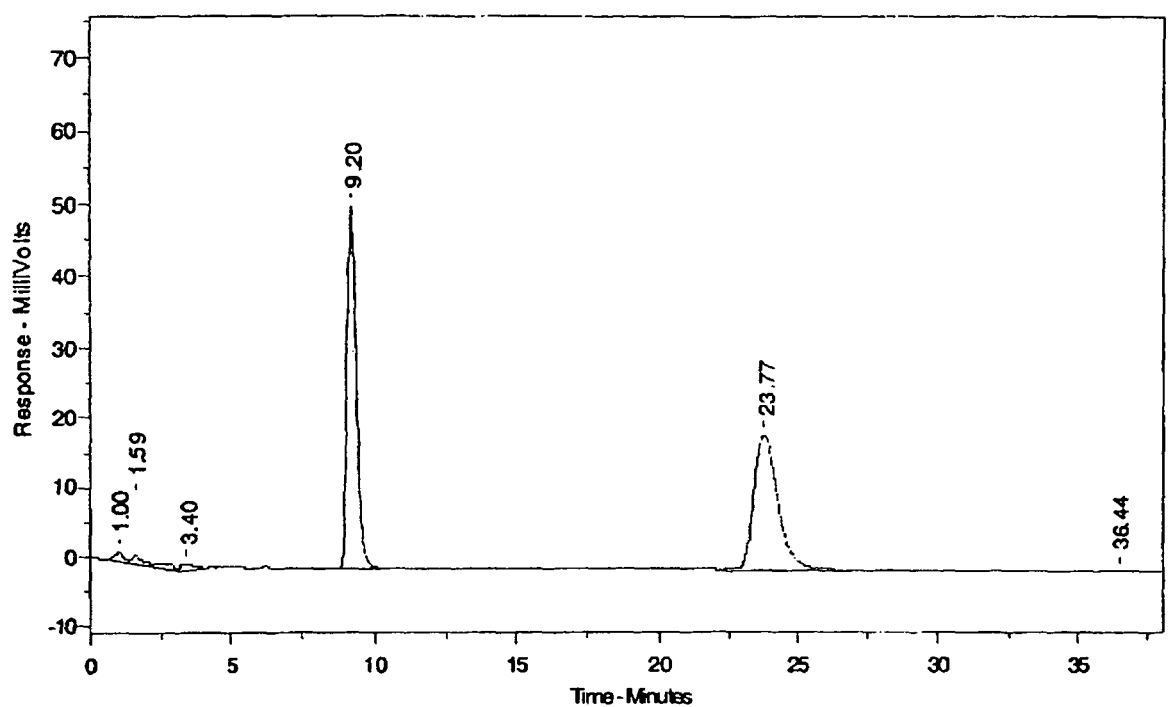
FIG. 11 is a chromatogram obtained in Example 9.

Resolution was performed by replacing the mobile phase of Example 3 by a hexane/chloroform (CHCl3)/diethylamine between the elution time (t1) of the first peak and a time (Gt) required for gradient by 6.5 (factor (f2)). Thus, favorable resolution was achieved. The results are shown in Table 5 and FIG. 11.

TABLE 5

| | Resolution under gradient conditions | | | | | Ratio (B) obtained by converting CHCl3 ratio at the time of completion of gradient in terms of isocratic | Factor (f2) | Resolution under isocratic conditions | | | |
|---|---|---|---|---|---|---|---|---|---|---|---|
| | | | | Ratio at the time of the elution of the first peak (Hexane/*CHCl3/DEA) | Example | | | Mobile phase (Hexane/ CHCl3/DEA) | T1 (min) | T2 (min) | a |
| Compound | T1 (min) | T2 (min) | a | | | | | | | | |
| Aminoglutethimide | 26.68 | 32.96 | 1.27 | 22/78/0.1 | Example 9 (FIG. 10) | 19 | 6.5 | 25/75/0.1 | 9.2 | 23.77 | 3.35 |

*Gradient solvent

INDUSTRIAL APPLICABILITY

According to the present invention, the success or failure of resolution can be simply and rapidly confirmed by applying the HPLC gradient elution analysis using a column for resolving optical isomers when resolution of optical isomers is performed. Further, when the resolution is achieved, the eluent composition under isocratic elution conditions can be easily estimated from the elution time of gradient elution analysis.

The invention claimed is:

1. A method of analyzing or resolving an optical isomer, comprising:
   resolving the optical isomer from a mixture of optical isomers by a gradient elution method using a solvent of two or more components and using a solvent-resistant column for resolving an optical isomer for use in HPLC in which a polysaccharide derivative is used as an asymmetry recognition agent and based on an elution time of a first peak (t1) obtained by a gradient analysis, resolving an optical isomer under isocratic conditions and at a composition ratio obtained by multiplying a solvent composition ratio at the time of t1 calculated from a gradient inclination factor (f1).

2. A method of analyzing or resolving an optical isomer according to claim 1, wherein the solvent for use in the gradient elution method comprises a solvent composition of two or more components containing a combination of a low polar solvent and a high polar solvent; a solvent composition of two or more components containing a combination of a low polar solvent and a medium polar solvent; a solvent composition of two or more components containing a combination of a medium polar solvent and a high polar solvent; or a solvent composition of three or more components containing a combination of a low polar solvent, a medium polar solvent, and a high polar solvent.

3. A method of analyzing or resolving an optical isomer according to claim 2, wherein, to the solvent for use in the gradient elution method, at least one of an amine compound and an acid compound is/are added in a proportion of 0.01 to 5.0%.

4. A method of analyzing or resolving an optical isomer according to claim 1, wherein the factor (f1) is within a range of from 0.8 to 0.1.

5. A method of analyzing or resolving an optical isomer according to claim 4, wherein the factor (f1) is within a range of from 0.5 to 0.1.

6. A method of analyzing or resolving an optical isomer, comprising: in a case where a compound is eluted after completion of gradient in claim 1,
   calculating a ratio under isocratic conditions by multiplying a solvent ratio at the time of completion of gradient by 0.2; and
   resolving an optical isomer under isocratic conditions and at a composition ratio obtained by multiplying a difference between an elution time (t1) of a first peak and a time (Gt) required for gradient by a factor (f2) to the ratio.

7. A method of analyzing or resolving an optical isomer according to claim 1, wherein the factor (f2) is within a range of from 4 to 30.

8. A method of analyzing or resolving an optical isomer according to claim 1, wherein the factor (f2) is within a range of from 5 to 20.

* * * * *

UNITED STATES PATENT AND TRADEMARK OFFICE
CERTIFICATE OF CORRECTION

| | | |
|---|---|---|
| PATENT NO. | : 7,758,753 B2 | Page 1 of 1 |
| APPLICATION NO. | : 12/226855 | |
| DATED | : July 20, 2010 | |
| INVENTOR(S) | : Atsushi Ohnishi et al. | |

It is certified that error appears in the above-identified patent and that said Letters Patent is hereby corrected as shown below:

On the title page, item (22), change the PCT filing date from "July 22, 2007" to -- June 22, 2007 --.

Signed and Sealed this

Nineteenth Day of October, 2010

David J. Kappos
*Director of the United States Patent and Trademark Office*